(12) United States Patent
Lasersohn

(10) Patent No.: US 7,144,407 B1
(45) Date of Patent: Dec. 5, 2006

(54) CARDIOVASCULAR INTRA AORTIC BALLOON PUMP CATHETER WITH HEAT EXCHANGE FUNCTION AND METHODS OF USE

(75) Inventor: Jack W. Lasersohn, East Hampton, NY (US)

(73) Assignee: Alsius Corporation, Irvine, CA (US)

( * ) Notice: Subject to any disclaimer, the term of this patent is extended or adjusted under 35 U.S.C. 154(b) by 832 days.

(21) Appl. No.: 10/160,138

(22) Filed: May 30, 2002

(51) Int. Cl.
*A61M 29/02* (2006.01)
*A61M 29/00* (2006.01)

(52) U.S. Cl. .................... 606/192; 606/194
(58) Field of Classification Search ........... 606/27, 606/28, 31, 192–194, 22, 25; 607/105–106; 604/94.01, 96.01
See application file for complete search history.

(56) References Cited

U.S. PATENT DOCUMENTS

| | | | |
|---|---|---|---|
| 5,106,360 A * | 4/1992 | Ishiwara et al. ............ 600/2 |
| 5,151,100 A * | 9/1992 | Abele et al. ............... 606/28 |
| 5,417,653 A * | 5/1995 | Sahota et al. .............. 604/20 |
| 5,865,721 A * | 2/1999 | Andrews et al. ............ 600/18 |
| 6,071,956 A * | 6/2000 | Slepian et al. ............ 514/496 |
| 6,126,684 A * | 10/2000 | Gobin et al. .............. 607/113 |
| 6,299,599 B1 * | 10/2001 | Pham et al. ............... 604/113 |

* cited by examiner

*Primary Examiner*—Michael Peffley
*Assistant Examiner*—Aaron Roane
(74) *Attorney, Agent, or Firm*—John L. Rogitz

(57) ABSTRACT

An intra-aortic balloon pump catheter system (apparatus and method) includes a pumping element for pumping a patient's blood and one or more heat exchange for exchanging heat with the patient's blood to provide efficient temperature control of the patient. The catheter may also provide access to the patient's central venous system through one or more infusion lumens and infusion ducts. An elongate body defines an inflation lumen that conveys an inflation fluid to and from the pumping element, and an inflow lumen and an outflow lumen that supply heat exchange fluid to and from each heat exchange element. The pumping element may include an everting pumping balloon that expands out of a cavity in the elongate body after insertion of the catheter. The catheter may have an internal heating element that heats or cools the heat exchange fluid.

19 Claims, 6 Drawing Sheets

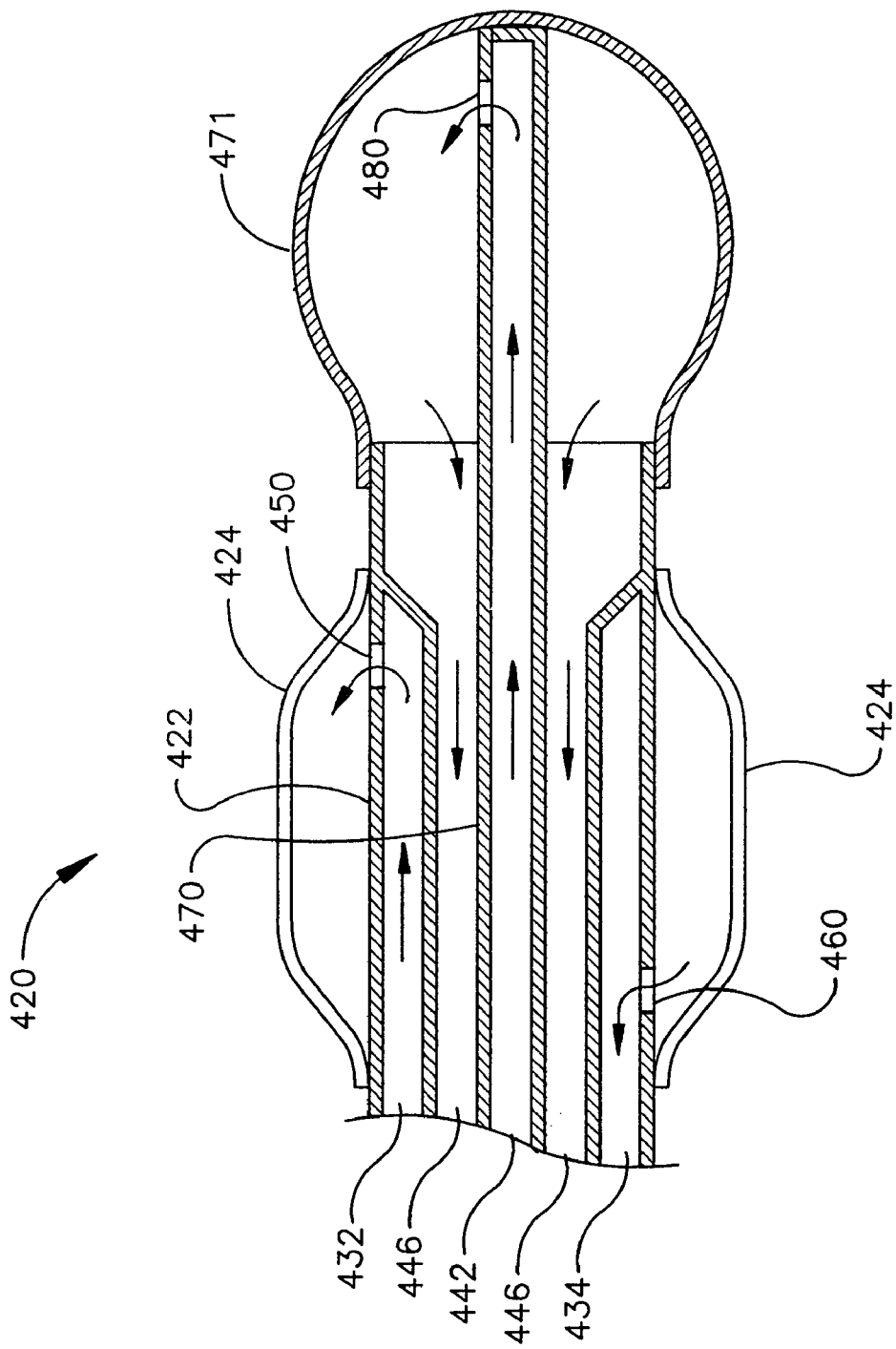

CARDIOVASCULAR INTRA AORTIC BALLOON PUMP CATHETER WITH HEAT EXCHANGE FUNCTION AND METHODS OF USE

BACKGROUND OF THE INVENTION

The field of the present invention is apparatus and methods for producing heat exchange with and assisting flow of a body fluid in a body conduit of a patient.

Intra-aortic balloon pump (IABP) catheters are used to assist a patient's heart in pumping blood through a patient's circulatory system. IABP catheters typically may be used in situations in which the pumping function of a patient's heart is impaired, and particularly during and/or following heart surgery.

An IABP catheter typically has an inflatable balloon at its distal end. The catheter is inserted into the patient's central venous system so that the balloon is located adjacent the patient's heart. The balloon is then inflated and deflated cyclically, and preferably in timing with the patient's heartbeat. As the balloon inflates and deflates, it provides a pumping function to help move blood through the patient's circulatory system.

In addition to using an IABP catheter to assist in pumping blood when a patient's heart function is impaired, it may be desirable to reduce the patient's body temperature below normal body temperature so that the patient experiences hypothermia. Many advantages of hypothermia are known. By way of example, it has been found desirable to lower body temperature to reduce the metabolism of the body. This has been particularly desirable in surgical applications where the reduced metabolism has made it possible to more easily accommodate lengthy operative procedures. In cases of stroke and several other pathological conditions, hypothermia also reduces the permeability of the blood/brain barrier. It inhibits release of damaging neurotransmitters and also inhibits calcium-mediated effects. Hypothermia also inhibits brain edema and lowers intracranial pressure. In the case of cardiac arrest, application of hypothermia has been shown to reduce myocardiac infarction as well as prevent or limit neurologic injury. Hypothermia has also been used during cardiac surgery with cardiopulmonary bypass as a means to protect the brain from ischemic injury. In other cases, it may be desireable to cool a patient experiencing a fever so that the patient's body temperature returns to normal.

In yet other situations, it may be desirable to raise the patient's body temperature. Such situations may occur once the application of hypothermia is no longer needed and it becomes desirous to warm the patient back to normal temperature. In another application, warming the patient may be needed if a patient's body drifts dangerously close to severe hypothermia. Control of a patient's temperature may be problematic during hospital stays and particularly during active interventions such as surgery. The patient's body temperature may drift too low during surgery, potentially being deterimental to the patient's health. Body temperature may be artificially maintained at a normothermic temperature (approximately 98.6° F.) during surgery and post-operatively.

Conventional therapies used to manage patient temperature include acetaminophen (Tylenol), cooling blankets, heating blankets such as warm water blankets, forced warm or cool air, heat lamps, endovascular catheters, ice packs, ice baths, cold or warm infusions, and cold saline rectal or gastric lavages. With some of the conventional therapies, the warming or cooling rates are restricted by the body's ability to resist surface cooling or heating with vasodilation and sweating. The conventional approaches to cooling a patient also may require additional steps, may require excessive time and may not provide for precise control of patient temperature over long periods of time. Further, some of these devices cover a significant portion of a patient's body, inhibiting access to the patient.

Other techniques for controlling patient temperature employ intravascular heat exchange catheters that may be inserted into the patient's circulatory system. A relatively cool or warm fluid may be circulated through such catheters in a closed loop and exchange heat with blood flowing in the circulatory system, and may improve the patient's medical outcome. Carrying out both the pumping function of an IABP catheter and the heat transfer function of a heat exchange catheter conventionally requires the use of two separate catheters. Compared with using a single catheter, using two catheters increases the complexity of the procedure and requires additional steps to be carried out.

SUMMARY OF THE INVENTION

It would be advantageous to provide both a heat transfer function and a pumping function in a single catheter to reduce the complexity of conventionally providing both functions and to permit both functions to be carried out simultaneously. The present invention is directed to an IABP catheter with an intravascular heat exchange function and methods for its use. A pumping element that aids blood flow is combined with one or more heat exchange elements to provide efficient temperature control of a patient, and to provide convenient access to the patient's central venous system with a single catheter.

In a first separate aspect of the invention, an IABP catheter comprises a pumping element that aids blood flow in a patient's circulatory system and a heat exchange element that exchanges heat with the patient's blood so that a single catheter carries out both a pumping function and a heat transfer function.

In a second separate aspect of the invention, an IABP catheter comprises a generally tubular elongate body defining an inflation lumen that conveys a fluid to and from the pumping element, and also defining an inflow lumen and an outflow lumen that supply heat exchange fluid to and from one or more heat exchange elements.

In a third separate aspect of the invention, an IABP catheter comprises a pumping element that includes an everting pumping balloon that is moveable between an insertion configuration in which the everting pumping balloon is at least partially contained in the elongate body to facilitate insertion of the catheter into a patient, and an operative configuration in which at least a substantial part of the everting pumping balloon is outside of the elongate body.

In a fourth separate aspect of the invention, an IABP catheter may include a moveable inner shaft that moves the everting pumping balloon between the insertion configuration and the operative configuration.

In a fifth separate aspect of the invention, an IABP catheter is provided with multiple heat exchange balloons that are spaced along the elongate body to provide controlled and balanced heat transfer, and to provide the catheter with flexibility.

In a sixth separate aspect of the invention, an IABP catheter having a heat exchange function is provided with one or more infusion lumens and infusion ducts that provide communication between the catheter and the patient's circulatory system.

In a seventh separate aspect of the invention, an IABP catheter comprises a heating element that heats or cools the heat exchange fluid, and a generally tubular elongate body defining an inflation lumen that conveys a fluid to and from a pumping element, and also defining a flow lumen that conveys heat exchange fluid to and from one or more heat exchange elements.

In an eighth separate aspect of the present invention, it is contemplated that combinations of the foregoing separate aspects may be incorporated into a single embodiment.

Therefore, it is an object of the present invention to provide an IABP catheter with a heat exchange function and methods for its use. Other and further objects and advantages will appear hereafter.

BRIEF DESCRIPTION OF THE DRAWINGS

FIG. 1A is a cross-sectional view of the IABP catheter of FIG. 1;

FIG. 5 is a schematic side sectional view of a distal portion of a fifth embodiment of an IABP catheter with an everting pumping balloon in an operative configuration and a moveable inner shaft in an operative position;

DETAILED DESCRIPTION OF THE INVENTION

Figure 1:
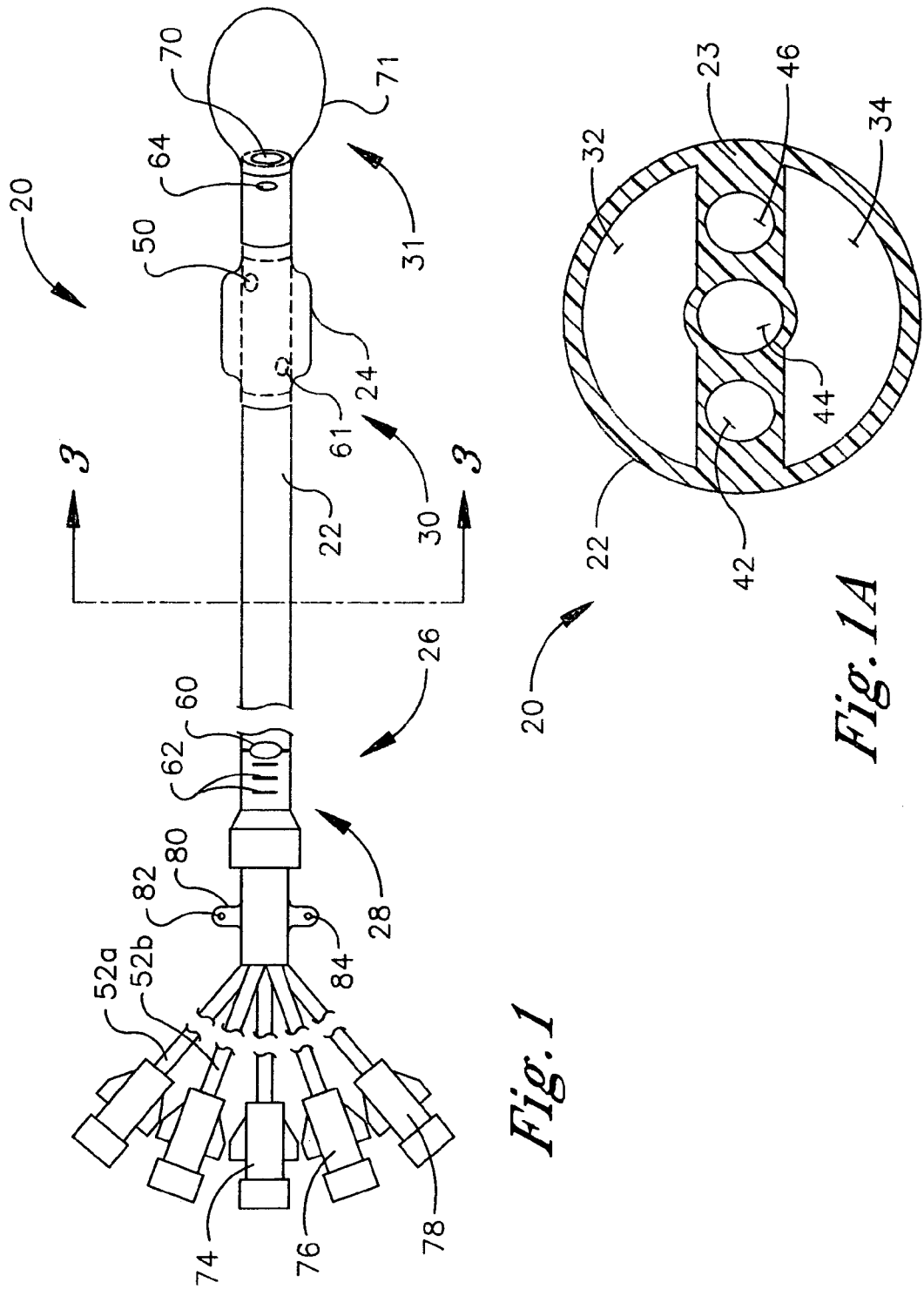
FIG. 1 is a schematic side elevational view of a first embodiment of an IABP catheter.

The preferred embodiments will be described with reference to drawing figures, wherein like reference numerals are applied to like elements.

U.S. Pat. Nos. 6,146,411, 6,126,684, and 6,165,207, each of which is hereby incorporated by reference, disclose systems employing catheters that may be inserted into the body of a patient to exchange heat with the blood supply of the patient. The indwelling catheters of the referenced patents are disposed in a heat exchange relationship with the blood supply, and a heat exchange fluid is circulated through the catheters in a closed loop. Outside the patient's body, the heat exchange fluid passes through a cooling or heating system to re-cool or re-heat the fluid. These catheters may change the patient's temperature and may thereby improve the patient's medical outcome.

The heat exchange capability and other advantages of the heat exchange catheters disclosed in the above-referenced patents may be implemented with an IABP catheter in the preferred embodiments here, so that a single device both accomplishes the functions of conventional IABP catheters and effectively manages patient temperature. By supplementing the known functions of a central venous line IABP catheter with the function of cooling or warming the patient's blood, a single catheter may be used to access to the venous system through a single, relatively small incision, reducing the risk of complications. The access, for example, through a femoral vein, a jugular vein or a subclavian vein, is to the central blood supply, via the central venous system, and is therefore particularly expedient, permitting efficient cooling or warming of a patient. The term central venous system generally relates to the portion of the venous system which returns blood to the right side of the heart, including the inferior and superior vena cava.

FIGS. 1 and 1A depict one embodiment of an IABP catheter 20 adapted to exchange heat with a body fluid flowing through a body conduit of a patient, such as blood in a patient's central venous system. The catheter 20 comprises an elongate body 22 having a substantially tubular configuration, a proximal portion 26 with a proximal end 28, and a distal portion 30 with a distal end 31. When operatively disposed, the distal end 31 is disposed within the patient's body, and the proximal end 28 is disposed outside of the patient's body.

A pumping element 71 preferably is sealingly connected with the elongate body 22 near the distal end 31. The pumping element 71 may be expanded and contracted to pump the patient's blood through the venous system. The pumping element 71 preferably comprises an inflatable balloon that is moveable between a deflated configuration and an inflated configuration such that the balloon's volume is increased. An inflation fluid (not shown) is moved into and out of the pumping element 71 to move the pumping element 71 between the deflated and inflated configurations. The flow of the inflation fluid is controlled by an external drive system (not shown) that receives information regarding the patient's heartbeat, such as blood pressure information, and pumps the inflation fluid in timing with the patient's heartbeat.

At least one heat exchange element 24, such as a fluid-carrying inflatable balloon, is disposed proximally of the pumping element 71 and extends at least partially along the implantable, distal portion 30 of the elongate body 22. For illustrative purposes, this embodiment is shown to have only one heat exchange element 24. Preferably, however, a catheter has more than one heat exchange element (as will be described below in connection with other embodiments), and may have numerous heat exchange elements.

Referring also to FIG. 1A, which is a cross-sectional view taken along line 3—3 of the catheter 20 of FIG. 1, the elongate body 22 includes an inflow lumen 32, an outflow lumen 34, an inflation lumen 42 and two auxiliary lumens 44, 46. The various lumens 32, 34, 42, 44, 46 extend between the proximal portion 26 and the distal portion 30 of the elongate body 22. External access to the inflation lumen 42 and two auxiliary lumens 44 46 is supplied by lumen fittings 74, 76, 78. External access to the inflow lumen 32 and outflow lumen 34 is provided by an inlet tube 52a and an outlet tube 52b.

Heat exchange fluid (not shown) flows through the elongate body and through the heat exchange element 24 to heat or cool a patient. The heat exchange fluid is supplied through the inflow lumen 32 and enters the heat exchange element 24 through an inflow duct 50, then flows through the heat exchange element 24, and exits through an outflow duct 61. The heat exchange fluid is remotely cooled or heated outside of the catheter 20, such as by a temperature control system (not shown), and is conveyed to and from the catheter 20 via the inlet tube 52a and the outlet tube 52b.

The particular heat exchange fluid selected is preferably biocompatible to avoid harm to the patient in the event of inadvertent rupture. Candidate materials include sterile saline and water, although other fluids having suitable viscosity, heat exchange and material compatibility characteristics can also be used.

The pumping element 71 is inflated and deflated with an inflation fluid. The inflation fluid is conveyed through an inflation lumen 42 extending through the elongate body 22. The inflation fluid enters the pumping element 71 through an inflation duct 70 and expands the pumping element 71. The inflation fluid then exits the pumping element 71 through the inflation duct 70 to deflate the pumping element 71. The cyclic inflation and deflation of the pumping element 71 pumps the patient's blood through the venous system.

Preferably, the inflation fluid comprises a gas, such as helium, so that the pumping element 71 may be inflated and deflated rapidly in timing with the patient's heartbeat. Alternately, the inflation fluid may comprise a liquid, such as saline or water. The liquid may have the same composition as the heat exchange fluid that circulates through the heat exchange element 24. Even if the inflation fluid has the same composition as the heat exchange fluid, however, the inflation fluid preferably is physically separated from the heat exchange fluid inside the elongate body 22. Separating the fluids permits the fluids to be pressurized to different degrees so that the pumping action of the pumping element 71 can be controlled independently of the flow of the heat exchange fluid.

The auxiliary lumens 44, 46 may serve one or more of a variety of functions, including providing a conduit for infusion of drugs such as chemotherapy, fluids and nutrition, providing access for syringes for sampling, and accommodating various sensors, such as a blood pressure sensors and thermistors to monitor the patient, thus generally providing access to the central blood supply as dictated by the particular application. The auxiliary lumens 44, 46 each preferably have a duct (not shown) that provides fluid communication between each auxiliary lumen 44, 46 and the outside surface of the catheter 20 so that the auxiliary lumens 44, 46 provide access to the body conduit in which the catheter 20 is inserted. The auxiliary lumens 44, 46 may also be configured to receive a guidewire, which may be used to stiffen the catheter 20 during insertion and removed after insertion.

Alternately, an auxiliary lumen 44, 46 may be configured as a deflation lumen to convey inflation fluid away from the pumping element 71 and through the elongate body 22. Unlike the auxiliary lumens described herein, the deflation lumen would not be in fluid communication with the outside of the catheter 20, but instead would be in fluid communication with the pumping element 71 through a deflation duct (not shown) similar in structure to the inflation duct 70. In such an embodiment, the catheter 20 would have an inflation lumen 42 for conveying the inflation fluid to the pumping element 71 and a separate deflation lumen for conveying the inflation fluid away from the pumping element 71, instead of having a single inflation lumen 42 through which inflation fluid may be conveyed both to and away from the pumping element 71. While the catheter 20 depicted in FIG. 1 has an inflation lumen 42 and two auxiliary lumens 44, 46, other numbers of auxiliary lumens are contemplated and may be suitable depending on the particular application.

The various lumens 32, 34, 42, 44, 46 may have different cross-sectional shapes and sizes. For example, the auxiliary lumen 44 in the center may have a larger diameter than the inflation lumen 42 and the other auxiliary lumen 46 in order to better support a guidewire. Unlike the embodiment shown, the inflation and auxiliary lumens 42, 44, 46 may each have a larger cross-sectional area than each of the inflow lumen 32 and outflow lumen 34.

The catheter 20 preferably is formed of a polymer material 23 that defines the various lumens 32, 34, 42, 44, 46. A preferred material 23 is polyurethane, although other materials, such as nylon, polyethylene, PEBAX, PVC, Tygon® or the like may also be used. Considerations in selecting the appropriate material 23 include biocompatibility, flexibility, temperature change compatibility, and resistance to buckling.

As shown in FIG. 1, one or more depth markings 60, 62 may be disposed on the elongate body 22 to indicate the length of a portion of the catheter 20 that is inserted into the patient. Preferably, the depth markings 60, 62 are disposed at least on the proximal portion 26 of the elongate body 22 so that they are visible when the catheter 20 is inserted into the patient. The markings 60, 62 may indicate a length of the catheter 20 measured from each marking 60, 62 to the distal end 31 of the catheter 20, or to the distal end of the inflated pumping element 71, and may be disposed at spaced intervals, such as one-centimeter intervals. Each marking 60, 62 may comprise any symbol that may be understood to represent a length or relative length or degree of intubation. One marking 60 is shown to comprise a numeral indicative of length (in centimeters, for example) from the marking 60 to the distal end 31 of the catheter. Other markings 62 may comprise dots, lines, hash marks or other marks.

The elongate body 22 may also include a distal indicator 64 that indicates the position of the distal end 31 of the elongate body 22. The distal indicator 64 preferably is disposed near the distal end 31 of the elongate body 22. The position of the distal indicator 64 inside the patient preferably may be determined using conventional medical technology, such as X-ray technology or fluoroscopy. Information regarding the position of the distal end 31 of the elongate body 22 may aid proper placement of the catheter 20, so that the catheter 20 is inserted to a degree that maximizes the heat transfer rate without harming the patient.

The catheter 20 preferably includes an anchor configured for affixing the catheter 20 to the patient. As shown in FIG. 1, the anchor may comprise a suture fitting 80. The suture fitting 80 can be made integrally with the catheter 20, or it can be made as a separate plastic fitting and engaged with the catheter 20. The suture fitting 80 includes two eyes 82, 84 through which sutures can be inserted and engaged with the patient or with a bandage or tape or other structure that is engaged with the patient. An anchor may be especially desirable in cases in which the catheter is inserted for an extended period.

The implanted portion of the catheter 20 may also be thromboresistant. The thromboresistant property may be provided, for example, in the form of a coating having thromboresistant characteristics. The coating may include an anticoagulant and/or be adapted to receive an electrical charge providing thromboresistance to the coating.

Figure 2:
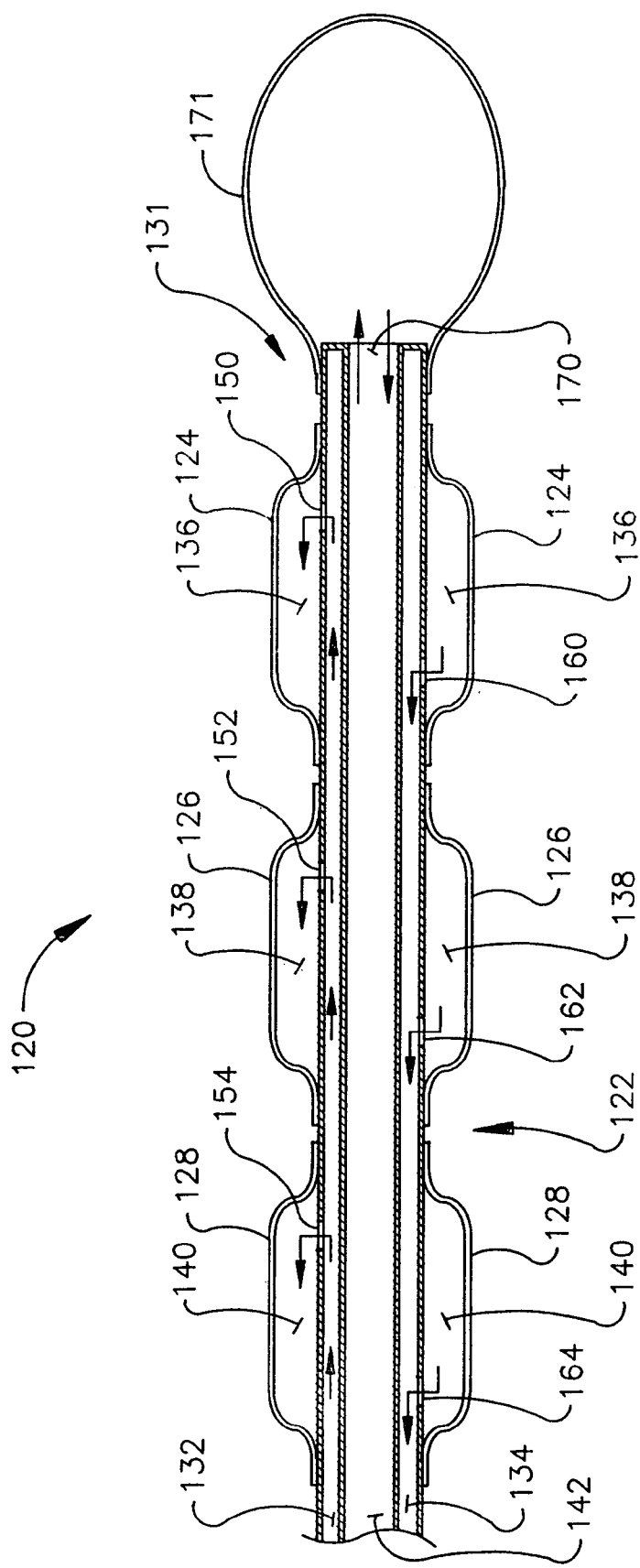
FIG. 2 is a schematic side sectional view of a distal portion of a second embodiment of an IABP catheter.

Although FIG. 1 depicts a catheter with a single heat exchange element, an IABP catheter may be provided with various numbers of heat exchange elements. FIG. 2 depicts a cross-section of a distal portion of a catheter 120 having three heat exchange elements 124, 126, 128. The principles described herein typically apply to catheters having any number of heat exchange elements.

A pumping element 171 extends distally from the distal end 131 of the elongate body 122. To expand the pumping element 171, inflation fluid is conveyed into the pumping element 171 (as indicated by the arrow) through an inflation lumen 142 and an inflation duct 170. To deflate the pumping element 171, the inflation fluid is conveyed out of the pumping element 171 (as indicated by the arrow), back through the inflation duct 170 and inflation lumen 142. Alternately, the inflation lumen 142 shown may be divided into two separate lumens to provide separate inflation and deflation lumens. Gravity, a pump, and/or a vacuum may be used to convey the inflation fluid through the inflation lumen 142. The elongate body 122 may also define auxiliary lumens like those described in connection with FIGS. 1 and 1A.

The three heat exchange elements 124, 126, 128 are disposed proximally of the pumping element 171. Each heat exchange element 124, 126, 128 preferably comprises a balloon that is inflatable from a deflated configuration, wherein the balloon lies substantially flush with the elongate body 122, to an operational configuration wherein the balloon is expanded away from the elongate body 122 by the pressure of the heat exchange fluid inside the balloon. The deflated configuration facilitates insertion and removal of the catheter 120, and the inflated configuration provides greater heat transfer capability.

Each heat exchange element 124, 126, 128 defines with the elongate body 122 a cavity 136, 138, 140. Heat exchange fluid (as indicated by the arrows) is circulated through the heat exchange elements 124, 126, 128 via the inflow lumen 132 and the outflow lumen 134. Heat exchange fluid introduced into the inflow lumen 132 flows through each inflow duct 150, 152, 154 and enters each cavity 136, 138, 140 of each heat exchange element 124, 126, 128. The heat exchange fluid flows through each heat exchange element 124, 126, 128 and exits each heat exchange element 124, 126, 128 through each outflow duct 160, 162, 164. The heat exchange fluid then flows through the outflow lumen 134 toward the proximal end of the catheter 120.

The inflow duct 150, 152, 154 of each heat exchange element 124, 126, 128 preferably is positioned distally of the corresponding outflow duct 160, 162, 164 to provide countercurrent flow, which facilitates the maximum heat exchange between the heat exchange fluid and the body fluid (e.g., blood). Further information regarding the structure, functions, positions and relative sizes of inflow ducts and outflow ducts is disclosed in U.S. Pat. No. 6,126,684.

The heat exchange fluid may be either relatively cool or relatively warm, depending on whether patient cooling or heating is desired. While in each cavity 136, 138, 140, the heat exchange fluid serves to provide a cold or warm fluid on an inner surface of each heat exchange element 124, 126, 128. With a body fluid, such as blood, flowing exteriorly of each heat exchange element 124, 126, 128, heat transfer occurs across each heat exchange element 124, 126, 128, effectively cooling or heating the body of the patient. The temperature of the heat exchange fluid is remotely controlled in order to achieve a desired patient target temperature or temperature range.

The pumping element 171 and each heat exchange element 124, 126, 128 each preferably comprise a balloon. Each balloon may be formed from a piece of flexible sheet material or extruded tubing formed into a molded balloon of the desired shape and size and then bound or otherwise fixed to the elongate body 122 to form each cavity 136, 138, 140. In one embodiment, each heat exchange element 124, 126, 128 is made of urethane, nylon, or polyethylene-terephthalate (PET) and is thin-walled, i.e., has a wall thickness of less than three mils, and more preferably less than one and one-half mils. The material make-up and wall thickness of the pumping element 171 may differ from that of the heat exchange elements 124, 126, 128. Further, the pumping element 171 and each heat exchange element 124, 126, 128 preferably are coated with an antimicrobial substance, as well as an anticlot substance, such as heparin.

One advantage of using multiple heat exchange elements 124, 126, 128 is that the flow and temperature of heat exchange fluid may be more readily controlled along the catheter 120 such that a more even and balanced transfer of heat can be achieved. Further, multiple heat exchange elements 124, 126, 128 may provide an increased surface area relative to embodiments having a single heat exchange element. Another advantage of using multiple heat exchange elements 124, 126, 128 is the ability of the catheter 120 to bend and flex when placed in a curved vasculature.

Figure 3A:
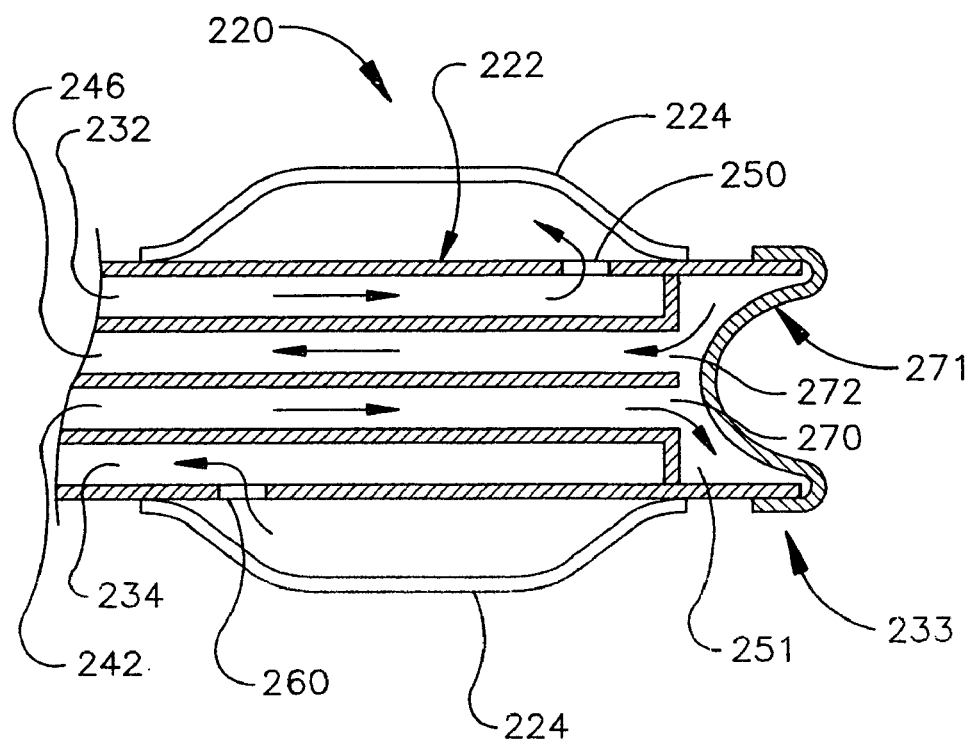
FIG. 3A is a schematic side sectional view of a distal portion of a third embodiment of an IABP catheter having an everting pumping balloon in an insertion configuration.
Figure 3B:
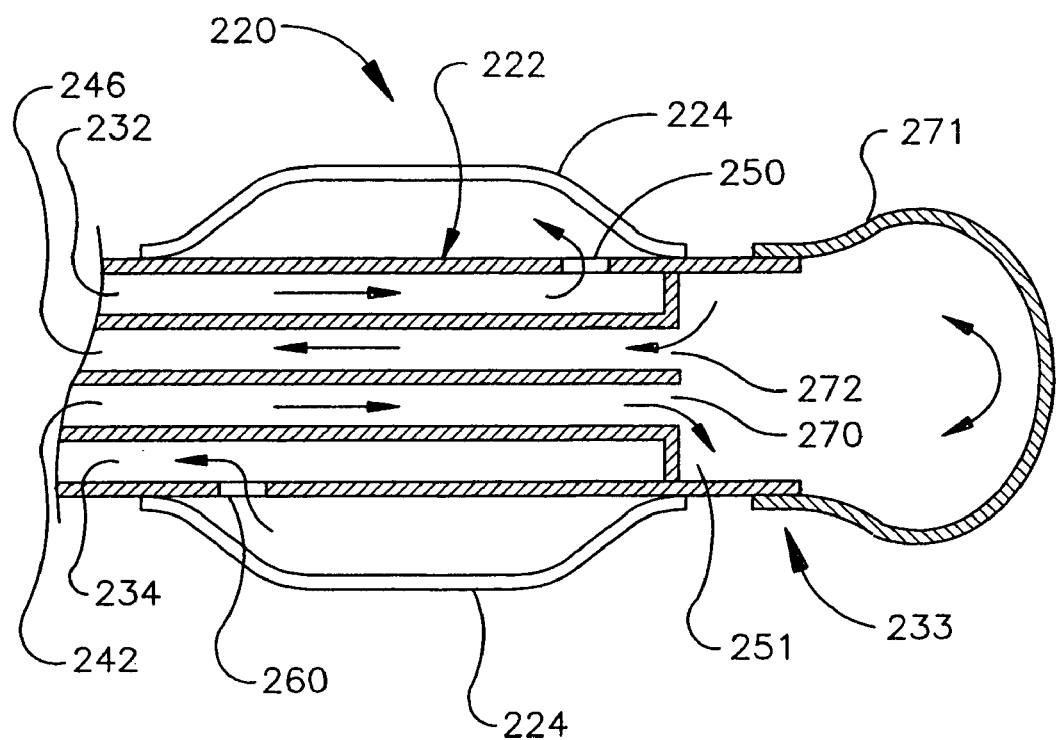
FIG. 3B is a schematic side sectional view of a distal portion of the IABP catheter of FIG. 3A with the everting pumping balloon in an operative configuration.

FIGS. 3A and 3B depict a distal portion of a catheter 220 with a pumping element that includes an everting pumping balloon 271. The everting pumping balloon 271 is moveable between an insertion configuration shown in FIG. 3A and an operative configuration shown in FIG. 3B. In the insertion configuration, the everting balloon 271 is at least partially contained inside the elongate body 222 to facilitate insertion and removal of the catheter 220. In the operative configuration, at least a substantial part of the everting balloon 271 is expanded outside of and preferably distally of the elongate body 222 to facilitate pumping of the patient's blood.

The everting pumping balloon 271 preferably sealingly engages the elongate body 222 near the distal end 233 of the elongate body 222. Part of the distal portion of the elongate body 222 preferably defines a cavity 251 that the everting pumping balloon 271 may enter. In the insertion configuration, the everting pumping balloon 271 is at least partially contained inside the cavity 251. Preferably, the distal portion of the catheter 220 is inserted into the patient with the balloon 271 in the insertion configuration shown in FIG. 3A. While in the insertion configuration, the balloon 271 is contained so as not to inhibit intubation, and is at least partially protected against potential damage during the intubation process, which may involve relatively high forces on the distal portion of the catheter 220.

Once the catheter 220 is inserted, the balloon 271 may be moved from the insertion configuration to the operative configuration shown in FIG. 3B. The balloon 271 may be moved from the insertion configuration toward the operative configuration by providing inflation fluid through the inflation lumen 242 and inflation duct 270 and into the balloon 271. As the inflation enters the balloon 271, the balloon 271 expands, and everts (or turns at least partially inside-out) while being pushed out of the cavity 251 in the elongate body 222. With the balloon 271 in the operative configuration, inflation fluid may be moved in and out of the balloon 271 to help pump the patient's blood.

In this embodiment, the catheter 220 has an inflation lumen 242 and inflation duct 270 through which inflation fluid is conveyed into the balloon 271 to inflate the balloon 271, as well as a separate deflation lumen 246 and deflation duct 272 through which inflation fluid is conveyed out of the balloon 271 to deflate the balloon 271. Alternately, inflation fluid may be conveyed both to and away from the balloon 271 through a single inflation lumen and the catheter 220 may have no deflation lumen 246 and no deflation duct 272.

The catheter 220 may also include auxiliary lumens (not shown). In embodiments having a deflation lumen 246, expansion of the balloon 271 may be aided if the deflation lumen 246 is blocked while inflation fluid flows through the inflation lumen 242.

In preparation for withdrawing the catheter 220 from the patient, the balloon 271 may be returned toward the insertion configuration shown in FIG. 3A to facilitate withdrawal and avoid damaging the balloon 271 or the patient's vasculature during withdrawal. The balloon 271 may be moved toward the insertion configuration by allowing inflation fluid to drain out of the balloon 271. Pressure in the deflation lumen 246 and/or inflation lumen 242 may be decreased to help draw the balloon 271 into the cavity 251 in the elongate body 222, such as by applying suction to both the deflation lumen 246 and inflation lumen 242 or applying suction to either lumen 246, 242 and blocking the other lumen 246, 242.

Although a single heat exchange element 224 is shown, the catheter 220 may include multiple heat exchange elements. A heat exchange fluid flows into the heat exchange element 224 through the inflow lumen 232 and inflow duct 250, and flows out of the heat exchange element 224 through the outflow duct 260 and outflow lumen 234.

Figure 4A:
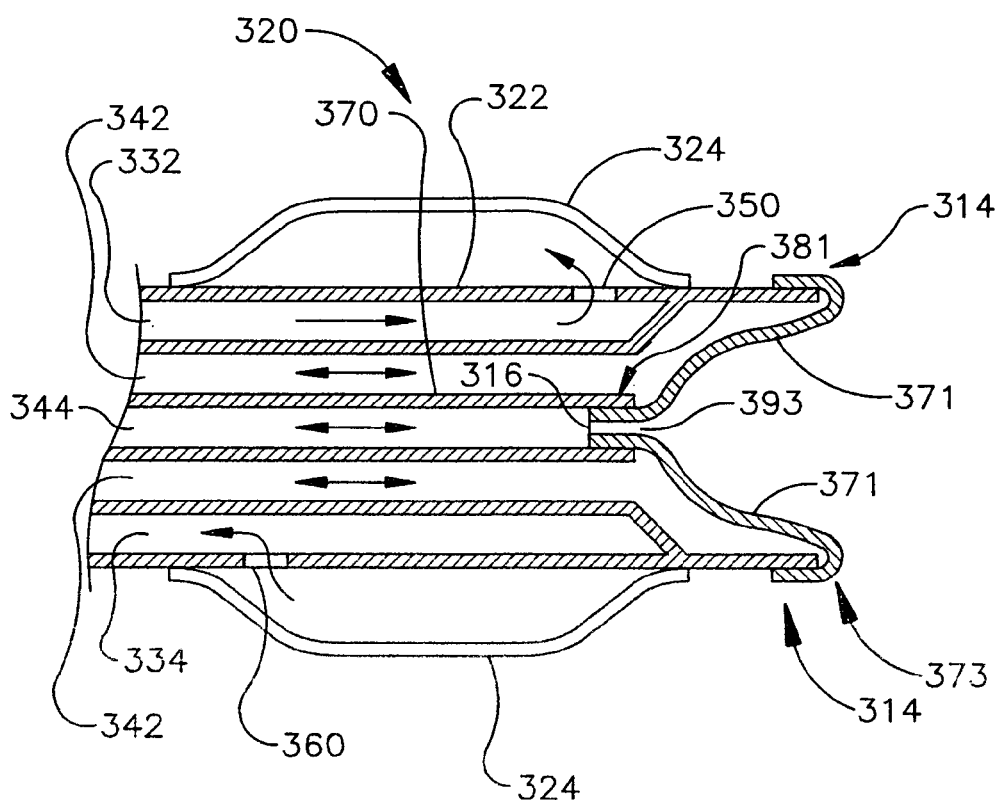
FIG. 4A is a schematic side sectional view of a distal portion of a fourth embodiment of an IABP catheter having an everting pumping balloon in an insertion configuration and a moveable inner shaft in an insertion position.
Figure 4B:
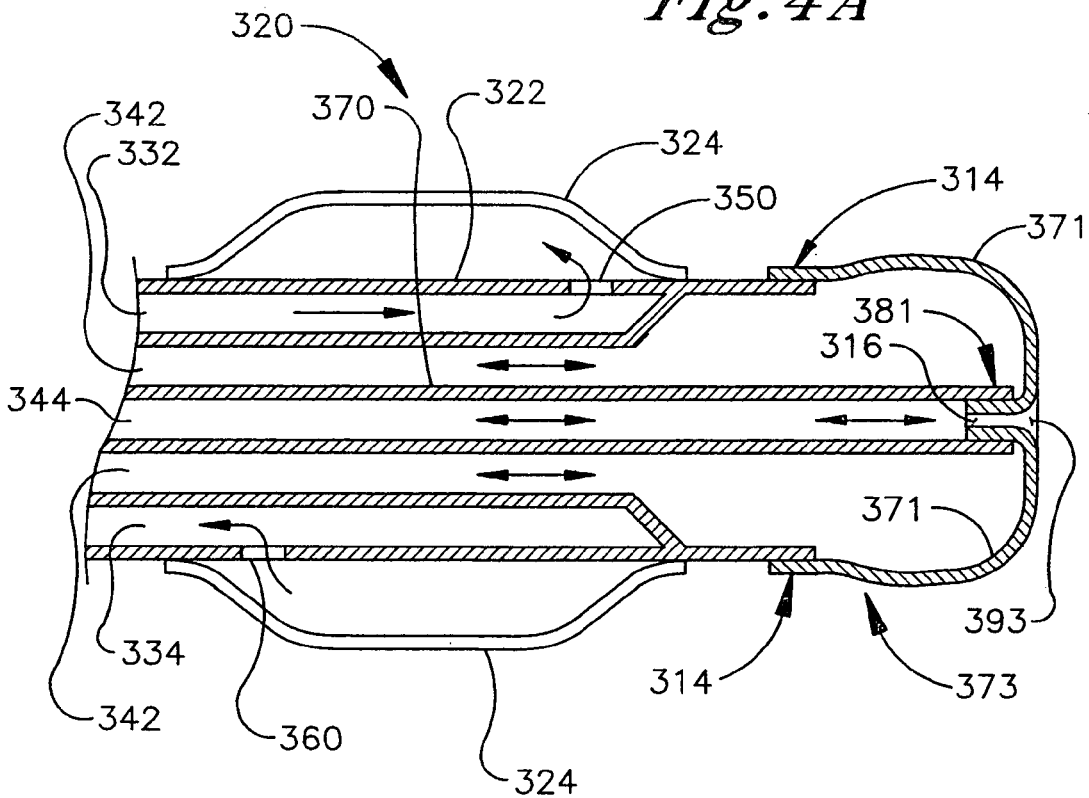
FIG. 4B is a schematic side sectional view of a distal portion of the IABP catheter of FIG. 4A with the everting pumping balloon in an operative configuration and the moveable inner shaft in an operative position.

As explained in connection with FIGS. 3A and 3B, the pressure of the inflation fluid may move the everting pumping balloon between the insertion and operative configurations. As shown in FIGS. 4A and 4B, a moveable inner shaft 370 may also, or alternately, be employed to move the everting pumping balloon 371 between the insertion configuration shown in FIG. 4A and the operative configuration shown in FIG. 4B.

In this embodiment, the inner shaft 370 is substantially coaxial with the elongate body 322, is positioned at least partially inside the elongate body 322, and is moveable within the elongate body 322. The inner shaft 370 has a distal shaft end 381 and defines an auxiliary lumen 344 and an auxiliary duct 393 that provide access to the central venous system through the catheter 320. An inflation lumen 342 is disposed in the space between the inner shaft 370 and the elongate body 322. Inflation fluid is supplied through the inflation lumen 342 to inflate the everting balloon 371, and is conveyed through the inflation lumen 342 in the opposite direction (away from the everting balloon 371) to deflate the balloon 371. Alternately, a deflation lumen (not shown) may also be provided, such as inside the inner shaft 370.

The inner shaft 370 is movable between an insertion position shown in FIG. 4A and an operative position shown in FIG. 4B. A first portion 314 of the everting pumping balloon 371 sealingly engages the distal end 373 of the elongate body 322, and a second portion 316 of the everting pumping balloon 371 sealingly engages the distal end 381 of the inner shaft 370.

In the operative position, the inner shaft 370 preferably extends distally of the distal end 373 of the elongate body 322. In moving from the insertion position to the operative position, the inner shaft 370 moves distally relative to the elongate body 322. As the shaft 370 is moved toward the operative position shown in FIG. 4B, it moves at least part of the everting pumping balloon 371 outside of the elongate body 322. With the pumping balloon 371 in the operative configuration, inflation fluid may be moved into and out of the balloon 371 to help pump the patient's blood.

Similarly to other embodiments, heat exchange fluid flows into a heat exchange element 324 through an inflow lumen 332 and inflow duct 350, flows through the heat exchange element 324, exchanges heat with the patient's blood to warm or cool the patient, and flows out of the heat exchange element 324 through an outflow duct 360 and outflow lumen 334.

As shown in FIG. 5, an everting pumping balloon 471 may be moved between insertion and operative configurations by a moveable shaft 470 with which the everting balloon 471 is not sealingly engaged. The inner shaft 470 may be pushed against the inside of the everting pumping balloon 471 to move the balloon 471 toward the operative configuration shown in FIG. 5. The everting balloon 471 sealingly engages the elongate body 420, but need not sealingly engage the shaft 470. Preferably, however, the balloon 471 is connected with the inner shaft 470 so that movement of the inner shaft 470 toward the insertion position pulls the balloon 471 toward the insertion configuration.

An inflation lumen 442 and inflation duct 480 are defined by the inner shaft 470. A deflation lumen 446 is defined between the inner shaft 470 and the elongate body 422. Inflation fluid is supplied through the inflation lumen 442 and inflation duct 480 to inflate the everting balloon 471, and is conveyed through the deflation lumen 446 away from the everting balloon 471 to deflate the balloon 471.

Heat exchange fluid may flow into a heat exchange element 424 through an inflow lumen 432 and inflow duct 450, flow through the heat exchange element 424 to exchange heat with the patient's blood, and flow out of the heat exchange element 424 through an outflow duct 460 and outflow lumen 434.

An IABP catheter preferably has a size (e.g., length and cross-sectional area) that maximizes the heat transfer rate without causing harmful physiological effects. It is believed that in at least some blood vessels, flow of blood through the vessel begins to be reduced when approximately 50% of the blood vessel cross section is blocked. To maintain blood flow, the cross-sectional size (e.g., diameter and/or area) of the catheter preferably is no more than approximately 30% to 75% of the cross-sectional size of the blood vessel in which the balloon is inserted, which will vary with the size of each patient's vasculature. This range may be modified to provide a suitable safety margin.

Various balloon configurations for the heat exchange elements may be employed, including but not limited to straight, helical, cylindrical, and fluted shapes. The particular configuration selected depends on the application and the desired heat exchange and other characteristics. Preferably, each heat exchange element has a configuration that safely maximizes the rate of heat transfer. The rate of heat transfer depends on many factors, such as the volumetric flow rates of the blood and the heat exchange fluid, the temperature difference between the heat exchange element and the blood, the thermal conductivity and thickness of the barrier between the two fluids, and the residence time of the heat transfer.

The rate of heat transfer may also depend partially on the geometry of the heat exchange element. Heat exchange may be enhanced when the heat exchange fluid is provided with well mixed flow. Mixing can be enhanced by providing an irregular surface next to which the heat exchange fluid flows, such as an irregular inner balloon surface or obstructions inside the heat exchange element. The configuration of the balloon itself, such as a spiral-shaped balloon, also may encourage mixing. Information regarding a spiral-shaped balloon residing within a straight balloon is disclosed in Applicant's patent application Ser. No. 10/045,936, which is hereby incorporated by reference as if fully set forth herein. Additional disclosures to heat exchange balloon shapes that may enhance fluid mixing is disclosed in Applicant's patent application Ser. No. 10/015,505, which is also hereby incorporated by reference as if fully set forth herein.

Although a heat exchange element may comprise a balloon, a heat exchange element alternately may have a different configuration, such as an array of flexible hollow fibers through which the heat exchange fluid is circulated. Further information regarding hollow fiber heat exchange elements and catheter systems having hollow fibers is disclosed in U.S. Pat. No. 6,165,207, which is hereby incorporated by reference as if fully set forth herein.

Figure 6:
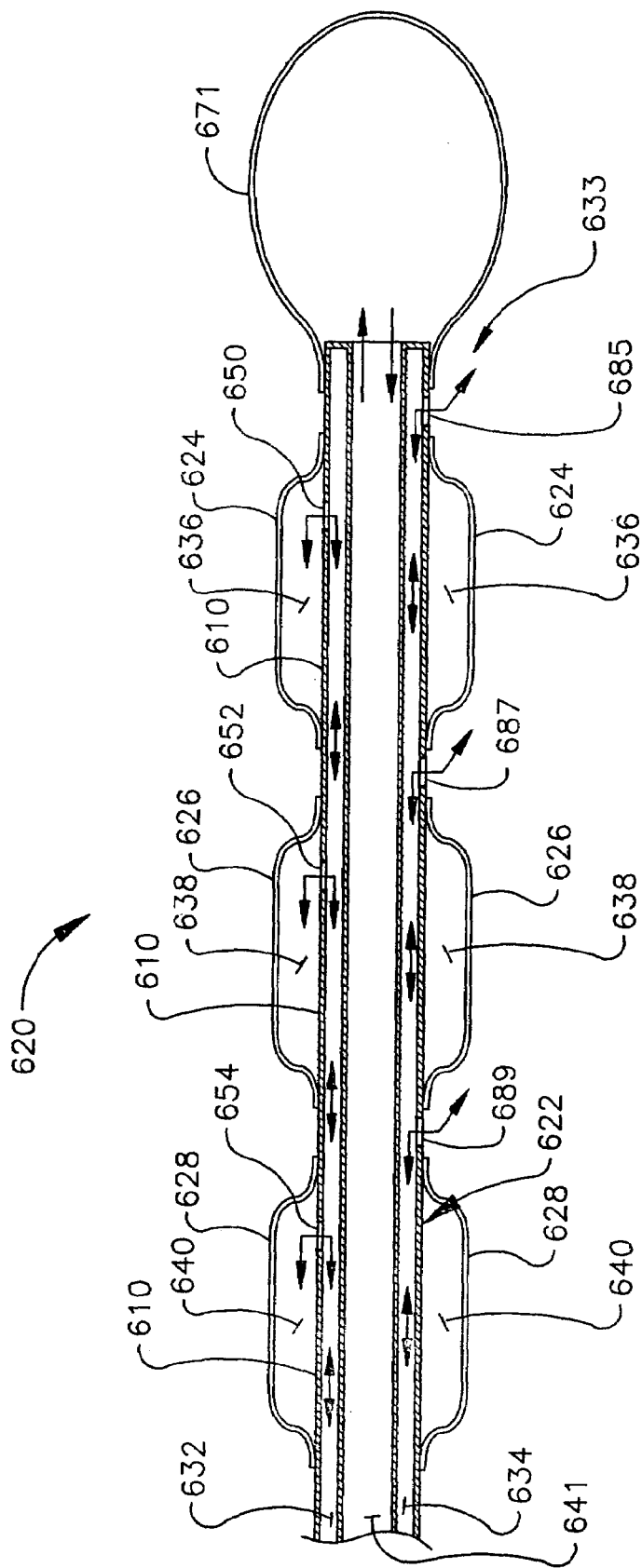
FIG. 6 is a schematic side sectional view of a distal portion of a sixth embodiment of an IABP catheter having a heating element.

In some embodiments, a heat exchange fluid is heated or cooled outside of the catheter and circulates through one or more heat exchange elements. As shown in FIG. 6, however, instead of circulating substantially continuously through each heat exchange element 624, 626, 628, the heat exchange fluid alternately may enter each heat exchange element 624, 626, 628 and remain in each heat exchange element 624, 626, 628 while being heated or cooled by a heating element 610. The heating element 610 may include a wire or other conductive material, a refrigerant, or other material that may be used to heat or cool the heat exchange fluid.

The heating element 610 preferably is disposed near the heat exchange elements 624, 626, 628 so that the heating element 610 may efficiently exchange heat with the heat exchange fluid inside the cavities 636, 638, 640 of the heat exchange elements 624, 626, 628. Preferably, the heating element 610 is embedded in or disposed along or near at least part of the distal portion of the elongate body 622.

A heat source (not shown) is used to heat or cool the heating element 610. The heat source preferably is located externally of the catheter 620 and is electrically, thermally or otherwise coupled with the heating element 610. The heat source may include an electrical source, a heater, a refrigerator, a laser, a radio frequency (RF) energy source, a microwave energy source, an ultrasonic energy source, or other source of heat transfer.

Because the heat exchange fluid is not continuously circulating through the heat exchange elements 624, 626, 628, separate inflow and outflow lumens are not needed. Instead, a single flow lumen 632 may be employed to deliver heat exchange fluid through flow ducts 650, 652, 654 both to and from the cavities 636, 638, 640 of the heat exchange elements 624, 626, 628. A pump or gravity may be used to move heat exchange fluid into the heat exchange elements 624, 626, 628. A pump, suction or gravity may be used to move heat exchange fluid out of the heat exchange elements 624, 626, 628. The structure and function of the flow lumen 632 and flow ducts 650, 652, 654 are similar to that of the inflow lumens and ducts and outflow lumens and ducts described in connection with other embodiments, except that the flow lumen 632 and flow ducts 650, 652, 654 are used to transport heat exchange fluid both to and from the heat exchange elements 624, 626, 628. An inflation lumen 641 and/or deflation lumen (not shown) conveys infusion fluid to and from a pumping element 671.

An infusion lumen 634 extends through the elongate body 622 and may communicate with the patient's body conduit through each of various infusion ducts 685, 687, 689 disposed on the elongate body 622. The infusion ducts 685, 687, 689 preferably are disposed adjacent to or between heat exchange elements 624, 626, 628.

Alternately, the catheter 620 may have three separate infusion lumens, each communicating with a single infusion duct 685, 687, 689. Providing multiple infusion lumens with infusion ducts that are spaced apart on a catheter allows, for example, the simultaneously delivery different medications to the patient at different locations in the patient's bloodstream, which may be especially desirable where mixing of the medications in relatively high concentrations is desired to be avoided.

Alternately, the catheter 620 of FIG. 6 may be configured without a heating element 610. In such an embodiment (not shown), the heat exchange fluid may be heated or cooled outside of the catheter and pumped into one or more heat exchange elements. The heat exchange fluid may remain in the heat exchange element, exchanging heat with the patient's tissue for some time (e.g., until the heat exchange fluid and adjacent tissue are nearly the same temperature), and then be removed from the heat exchange element. This process may then be repeated any number of times, the heat exchange fluid being re-heated or re-cooled outside of the catheter, and pumped back into the heat exchange element(s) to transfer heat with the patient's blood.

In accordance with a preferred method of use, the catheter may be inserted percutaneously through a puncture or surgical cut near the groin, on the chest area or neck area. Prior to insertion, the size (e.g., cross-sectional size and/or length) of the body conduit in which the catheter is to be inserted may be measured, and a catheter may be selected based on the size of the body conduit, so that the catheter maximizes the heat transfer rate without deleterious physiological effects on the patient.

Preferably, the catheter is inserted into the patient with the pumping element in the insertion configuration and with each heat exchange element being deflated and lying substantially flush with the elongate body. This configuration facilitates insertion of the catheter and avoids damaging the patient's vasculature during insertion.

In one preferred method of use, following this initial introduction, the catheter may be moved through the femoral and iliac veins, and into the inferior vena cava (IVC), of a patient. The catheter is preferably inserted into blood vessels of the lower central venous system, such as the femoral and iliac veins and the inferior vena cava (IVC), so that the pumping element may be positioned adjacent the patient's left ventricle to provide efficient pumping. Typically, the distal end of an IABP catheter is positioned in the ascending/descending aorta, which is the vein carrying blood from the patient's left ventricle. Further, the volume of the lower central venous system is greater than that of the upper central venous system jugular or subclavian, innominate, and superior vena cava), allowing a larger catheter (in both length and cross-sectional size) to be used. Alternately, however, the catheter systems disclosed herein may be used in the upper central venous system or introduced through the subclavian or jugular veins of the patient.

When operatively disposed, the distal end of the catheter is disposed within the patient's central venous system, and the proximal end is disposed outside of the patient's body. Once inserted in the patient, an IABP catheter may be used to help pump blood through the patient's circulatory system, and general access to the central blood supply is gained, enabling heat transfer, delivery of drugs, infusion fluids or nutrition, along with the gathering of patient blood for blood gas analysis and the like.

The pumping element may be moved from the insertion configuration to the operative configuration using the pressure of the inflation fluid and/or a moveable inner shaft. Inflation fluid may be moved into and out of the pumping element to expand and contract the pumping element and help pump the patient's blood. Each heat exchange element may be inflated with heat exchange fluid that is circulated through each heat exchange element to exchange heat with the patient's blood.

To facilitate removal of the catheter from the patient, the pumping element preferably is moved to the insertion configuration by removing inflation fluid from the pumping element and/or by moving the inner shaft to the insertion position. Each heat exchange element preferably is deflated by removing heat exchange fluid from each heat exchange element, such as by applying a suction to the inflow lumen and/or outflow lumen.

The catheter systems disclosed herein may be used in connection with systems for treating cardiac arrest that are disclosed in U.S. Pat. No. 6,149,670, which is hereby incorporated by reference as if fully set forth herein.

While the present invention has been described in terms of the preferred embodiments, other variations which are within the scope of the invention as defined in the claims will be apparent to those skilled in the art.

What is claimed is:

1. An intra-aortic balloon pump catheter adapted to exchange heat with a body fluid in a body conduit of a patient, the intra-aortic balloon pump catheter comprising:
   an elongate body including an inflow lumen, an outflow lumen and an inflation lumen each extending through the elongate body;
   a pumping element in fluid communication with the inflation lumen, the pumping element containing inflation fluid, the inflation fluid moving the pumping element in timing with the heartbeat of the patient when the catheter is operatively engaged with the patient; and
   a first heat exchange element in which a heat exchange fluid may flow, the first heat exchange element being in fluid communication with the inflow lumen and the outflow lumen.

2. The intra-aortic balloon pump catheter of claim 1, the elongate body further including a deflation lumen in fluid communication with the pumping element.

3. The intra-aortic balloon pump catheter of claim 1, the pumping element sealingly engaging the elongate body and extending from a distal end of the elongate body, the first heat exchange element disposed proximally to the pumping element and movable between a deflated configuration substantially flush with the elongate body and an inflated configuration in which the first heat exchange element is inflated outwardly from the elongate body by the heat exchange fluid.

4. The intra-aortic balloon pump catheter of claim 1, the catheter further comprising a second heat exchange element disposed proximally to the first heat exchange element and movable between a deflated configuration substantially flush with the elongate body and an inflated configuration in which the second heat exchange element is inflated outwardly from the elongate body by the heat exchange fluid.

5. The intra-aortic balloon pump catheter of claim 4, the pumping element including a pumping balloon movable between an insertion configuration in which the pumping balloon is at least partially contained inside the elongate body, and an operative configuration in which at least a substantial part of the pumping balloon is outside of the elongate body.

6. The intra-aortic balloon pump catheter of claim 1, the elongate body further including an infusion lumen extending therethrough.

7. The intra-aortic balloon pump catheter of claim 1, the catheter further comprising:
   a heating element for transferring heat with the heat exchange element; and
   a heat source for heating or cooling the heating element.

8. An intra-aortic balloon pump catheter of claim 7, the heat source including one or more of a group including an electrical source, a heater, a refrigerator, an air compressor, a laser, an RF energy source, a microwave energy source, and an ultrasonic energy source.

9. The intra-aortic balloon pump catheter of claim 1, the pumping element including a pumping balloon movable between an insertion configuration in which the pumping balloon is at least partially contained inside the elongate body, and an operative configuration in which at least a substantial part of the pumping balloon is outside of the elongate body.

10. An intra-aortic balloon pump catheter adapted to exchange heat with a body fluid in a body conduit of a patient, the intra-aortic balloon pump catheter comprising:
    an elongate body including inflow means for conveying a heat exchange fluid toward a distal portion of the elongate body, outflow means for conveying the heat exchange fluid toward a proximal portion of the elongate body, and inflation means for conveying an inflation fluid through the elongate body;
    pumping means for moving the body fluid in the body conduit in timing with the heartbeat of the patient when the catheter is operatively engaged with the patient, the pumping means being in fluid communication with the inflation means; and
    heat exchange means for exchanging heat between the heat exchange fluid and the body fluid in the patient's body conduit, the heat exchange means being in fluid communication with the inflow means and the outflow means.

11. The intra-aortic balloon pump catheter of claim 10, the catheter further comprising:
    heating means for transferring heat with the heat exchange means; and
    heat source means for heating or cooling the heating means.

12. The intra-aortic balloon pump catheter of claim 10, the elongate body further including infusion means for infusing an infusion fluid into the patient's body conduit.

13. A method for controlling a temperature of a patient and moving a body fluid through a body conduit of the patient, comprising the acts of:
    providing an intra-aortic balloon pump catheter comprising an elongate body, at least one heat exchange element, and a pumping element, and
    placing the pumping element in the body conduit;
    changing the volume of the pumping element to effect movement of the body fluid in the body conduit in timing with the patient's heartbeat;
    placing the at least one heat exchange element in a heat exchange relationship with the body fluid in the body conduit; and
    providing heat transfer with the at least one heat exchange element such that the heat exchange element is heated or cooled.

14. The method of claim 13, the step of changing the volume of the pumping element including the steps of moving an inflation fluid into the pumping element and moving the inflation fluid out of the pumping element.

15. The method of claim 13, the step of providing heat transfer with the at least one heat exchange element including the step of circulating a heat exchange fluid through the at least one heat exchange element to effect heat transfer with the body fluid in the body conduit.

16. The method of claim 13, the step of placing the pumping element in the body conduit including the step of moving the pumping element from an insertion configuration at least substantially inside the elongate body to an operative configuration at least substantially outside of the elongate body.

17. The method of claim 16, the catheter further comprising an inner shaft moveable within the elongate body, and the step of moving the pumping element including the step of moving the inner shaft distally relative to the elongate body.

18. The method of claim 13, the catheter further comprising at least one infusion lumen, the method further comprising the step of infusing a fluid into the body conduit via the at least one infusion lumen.

19. The method of claim 13, further comprising the step of:
   sensing a patient's blood pressure; and
   the step of changing the volume of the pumping element being carried out depending at least in part on the sensed blood pressure.

* * * * *